United States Patent [19]

Martin et al.

[11] Patent Number: 5,705,492
[45] Date of Patent: Jan. 6, 1998

[54] 3'-O-AMINOACYL ARA URIDINES, METHOD OF MAKING, AND ANTIVIRAL ACTIVITY

[75] Inventors: Joseph Armstrong Martin, Harpenden; Gareth John Thomas, Welwyn, both of England

[73] Assignee: Hoffmann-La Roche Inc., Nutley, N.J.

[21] Appl. No.: 677,705

[22] Filed: Jul. 10, 1996

[30] Foreign Application Priority Data

Jul. 13, 1995 [GB] United Kingdom ............... 9514267
Mar. 25, 1996 [GB] United Kingdom ............... 9606264

[51] Int. Cl.$^6$ .......................... A61K 31/70; C07H 19/09
[52] U.S. Cl. ........................ 514/50; 514/50; 536/27.11; 536/27.4; 536/28.54
[58] Field of Search .................. 514/50; 536/27.11, 536/27.4, 28.54

[56] References Cited

U.S. PATENT DOCUMENTS 4,851,519  7/1989  Lambert et al. ............... 536/28.2
5,010,060  4/1991  Lambert et al. ............... 514/49

FOREIGN PATENT DOCUMENTS 0 080 305  6/1983  European Pat. Off. .
257 378    8/1987  European Pat. Off. .

Primary Examiner—John Kight
Assistant Examiner—L. Eric Crane
Attorney, Agent, or Firm—George W. Johnston; Patricia S. Rocha-Tramaloni

[57] ABSTRACT

Pyrimidine nucleoside derivatives of formula

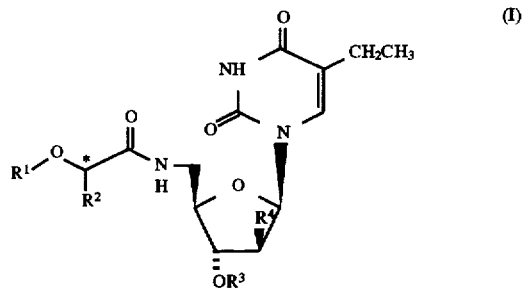

wherein $R^1$ represents aryl, $R^2$ represents lower alkyl, $R^3$ represents an acyl group derived from an amino acid and $R^4$ represents hydrogen or fluorine and the asterisk denotes that the configuration at the carbon atom indicated thereby is (S) or (R), are disclosed. These compounds, as well as their salts, are useful as antiviral agents.

14 Claims, No Drawings

3'-O-AMINOACYL ARA URIDINES, METHOD OF MAKING, AND ANTIVIRAL ACTIVITY

SUMMARY OF THE INVENTION

The present invention is concerned with pyrimidine nucleoside derivatives, a process for their manufacture and pharmaceutical preparations which contain these nucleosides.

DETAILED DESCRIPTION OF THE INVENTION

The pyrimidine nucleoside derivatives provided by the present invention are compounds of the general formula

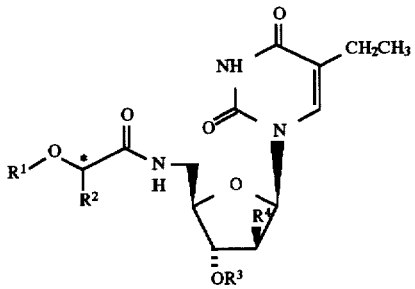

(I)

wherein $R^1$ represents aryl, $R^2$ represents lower alkyl, $R^3$ represents an acyl group derived from an amino acid, $R^4$ represents hydrogen or fluorine and the asterisk denotes that the configuration at the carbon atom indicated thereby is (S) or (R), and pharmaceutically acceptable acid addition salts thereof.

The compounds of the present invention are similar to those described in EP-A-257 378. Note, however, that in the compounds of the '378 application, $R^3$ is inter alia, an acyl group derived from an aliphatic, cycloaliphatic, araliphatic or aromatic carboxylic acid and not an acyl group derived from an amino acid.

The compounds of formula I and their pharmaceutically acceptable acid addition salts have valuable pharmacological properties. In particular, they inhibit viral thymidine kinase and are accordingly useful in the treatment or prophylaxis of viral infections, especially those caused by herpes simplex virus (HSV). In addition, they also have excellent solubility in aqueous media.

As used herein, the term "aryl" means unsubstituted phenyl or phenyl substituted by one or more halogen atoms, i.e. fluorine, chlorine, bromine or iodine atoms, and/or lower alkyl, lower alkoxy, aryl, trifluoromethyl or nitro groups, e.g. 4-chlorophenyl, p-tolyl, 4-methoxyphenyl, 2,4-dichlorophenyl, 2,4-dichloro-5-methoxyphenyl and the like.

The term "lower alkyl" means a straight-chain or branched-chain alkyl group containing 1–4 carbon atoms, e.g. methyl, ethyl, n-propyl isopropyl, n-butyl and the like.

The term "lower alkoxy" means a lower alkyl group as hereinbefore defined which is attached via an oxygen atom, e.g. methoxy, ethoxy, n-propoxy, isopropoxy, n-butoxy and the like.

Amino acids from which an acyl group denoted by $R^3$ in formula I is derived are preferably α-amino acids, which can be not only natural but also non-natural, e.g. glycine, alanine, valine, leucine, isoleucine, norleucine, phenylalanine, tyrosine, serine, cysteine, cystine, threonine, methionine, tryptophan, proline, 3- or 4-hydroxy-proline, asparagine, glutamine, ornithine, arginine, lysine, aspartic acid, glutamic acid, sarcosine and the like. However, other amino acids from which $R^3$ can be derived include β-amino acids such as β-alanine.

It will be appreciated that the compounds of formula I can exist as optically pure diastereomers or as mixtures of such diastereoisomers and that the invention includes within its scope not only each of the individual diastereomers, but also mixtures of such diastereomers.

Preferred compounds of formula I are those in which $R^1$ represents phenyl substituted by one or more substituents which may be the same or different, preferably by halogen and lower alkoxy, especially 2,4-dichloro-5-methoxyphenyl. $R^2$ preferably represents methyl. Preferably, $R^3$ represents an acyl group derived from a natural α-amino acid, especially L-valyl. $R^4$ preferably represents fluorine. Further, the configuration at the carbon atom indicated by the asterisk is preferably (S).

1-[5-[2(S)-(2,4-Dichloro-5-methoxyphenoxy)-propionamido]-2,5-dideoxy-2-fluoro-3-O-L-valyl-β-D-arabinofuranosyl]-5-ethyluracil is an especially preferred compound of formula I.

Other preferred compounds of formula I are:

1-[5-[2(S)-(2,4-Dichloro-5-methoxyphenoxy)-propionamido]-2,5-dideoxy-2-fluoro-3-O-D-valyl-β-D-arabinofuranosyl-5-ethyluracil, 1-[5-[2(S)-(2,4,6-trichloro-3-methoxyphenoxy)propionamido]-2,5-dideoxy-2-fluoro-3-O-L-valyl-β-D-arabinofuranosyl-5-ethyluracil, 1-[5-[2(S)-(2,4-dibromo-5-methoxyphenoxy)-propionamido]-2,5-dideoxy-2-fluoro-3-O-L-valyl-β-D-arabinofuranosyl-5-ethyluracil, and 1-[5-[2(R)-(2,4-dichloro-5-methoxyphenoxy)-propionamido]-2,5-dideoxy-2-fluoro-3-O-L-valyl-β-D-arabinofuranosyl-5-ethyluracil.

According to the process provided by the present invention, the compounds of formula I and their pharmaceutically acceptable acid addition salts are manufactured by reacting a compound of the general formula

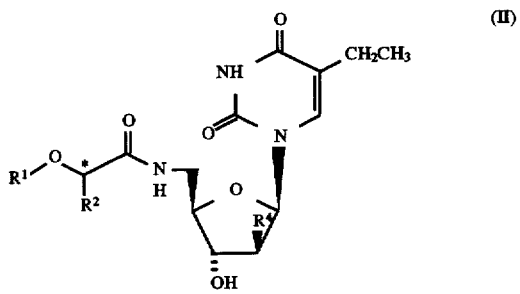

(II)

wherein $R^1$, $R^2$ and $R^4$ and the asterisk have the significance given earlier, with an N-protected amino acid and subsequently cleaving off the N-protecting group and, if desired, converting the compound of formula I obtained into a pharmaceutically acceptable acid addition salt.

The reaction of a compound of formula II with an N-protected amino acid is an acylation which can be carried out using reagents, solvents, protecting groups and methods for the removal of such protecting groups, all of which are well known to a person skilled in the art. In a preferred embodiment, a compound of formula II is reacted with an amino acid which is N-protected by tert.-butoxy-carbonyl (Boc) in the presence of ethyl dimethylaminopropyl carbodiimide hydrochloride and 4-dimethylaminopyridine and the subsequent deprotection is carried out by treatment with hydrogen chloride.

Compounds of formula I can be converted into pharmaceutically acceptable acid addition salts by treatment with an appropriate inorganic or organic acid according to procedures which are also well known in the art. Examples of such acids are hydrohalic acids, e.g. hydrochloric acid and hydrobromic acid, sulphuric acid, nitric acid, phosphoric acid, formic acid, acetic acid, citric acid, fumaric acid, malic acid, maleic acid, succinic acid, tartaric acid, methanesulphonic acid, benzene-sulphonic acid, toluenesulphonic acid, and the like.

The starting materials having formula II above are known compounds or are analogues of known compounds, which analogues can be prepared in analogy to the known compounds or to the detailed Example given hereinafter.

As is demonstrated below, the compounds of formula I and their pharmaceutically acceptable salts are useful as antiviral agents. The activity, of the compounds of formula I can be demonstrated on the basis of the following test procedure for the inhibition of HSV-2 thymidine kinase, a standard assay used to assess viral inhibition (Honess, et al., J. Gen. Virol., 58:237-249 (1982)).

In this test procedure, the assay mixture contains 50 mmol Tris HCl, pH 8, 5 mmol magnesium chloride, 5 mmol ATP, 0.3 μmol $^3$H-thymidine (50 Ci/mmol), suitably diluted enzyme preparation and various concentrations of test compounds in a total volume of 100 μl. Assays are incubated at 37° C. for 30 minutes and the reaction is terminated by immersion in a boiling water bath for 2 minutes. 85 μl aliquots from each assay are then dried on to DEAE-cellulose paper discs and the unphosphorylated $^3$H-thymidine is removed by washing in 4 mmol ammonium formate. The radioactivity remaining bound to the discs is then measured by scintillation spectrophotometry. The degree of inhibition at each concentration of test compound is expressed as a percentage of the control reaction (100%) after subtracting a measured blank value which represents the amount of radioactivity bound to the disc from a reaction containing heat-inactivated enzymes. The $IC_{50}$ value, namely the concentration of test compound which inhibits enzyme activity by 50%, is then calculated.

In the foregoing test, 1-[5-[2(S)-(2,4-dichloro-5-methoxy-phenoxy)-propionamido]-1,5-dideoxy-2-fluoro-3-O-L-valyl-β-D-arabinofuranosyl]-5-ethyluracil has an $IC_{50}$ of 1.1 nmol against HSV-2 thymidine kinase and 18 nmol against HSV-1 thymidine kinase.

The compounds of formula I and their pharmaceutically acceptable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically acceptable acid addition salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or anti-oxidants. They can also contain still other therapeutically valuable substances.

Medicaments containing a compound of formula I or a pharmaceutically acceptable acid addition salt thereof and a therapeutically inert excipient are also an object of the present invention, as is a, process for the production of such medicaments which comprises bringing one or more compounds of formula I or pharmaceutically acceptable acid addition salts thereof and, if desired, one or more other therapeutically valuable substances into a galenical administration form together with a compatible pharmaceutical carrier.

As mentioned earlier, the compounds of formula I and their pharmaceutically acceptable acid addition salts can be used in accordance with the invention as therapeutically active substances, especially as antiviral agents. The dosage can vary within wide limits and will, of course, be fitted to the individual requirements in each particular case. In general, in the case of administration to adults (weighing approximately 75 kg) a daily dosage of about 1 mg to 1000 mg, preferably about 5 mg to 500 mg or about 50 mg to 235 mg, should be appropriate. The daily dosage may be administered as a single dose or in divided doses.

Finally, the use of compounds of formula I and their pharmaceutically acceptable acid addition salts for the production of medicaments, especially of antiviral medicaments, is also an object of the invention.

The following Examples are intended to illustrate the present invention in more detail, but are not intended to limit its scope in any manner.

EXAMPLE 1

(A) 30.0 g (0.058 mol) of 1-[5-[2(S)-(2,4-dichloro-5-methoxy-phenoxy)-propionamido]-2,5-dideoxy-2-fluoro-β-D-arabino-furanosyl]-5-ethyluracil, 25.0 g (0.115 mol) of N-Boc-L-valine and 1 l of anhydrous dimethylformamide were placed in a 3 l four-necked flask. The solution was stirred under nitrogen and cooled to 10° C. in an ice bath. 7.04 g (0.058 mol) of 4-dimethylaminopyridine and 22.1 g (0.115 mol) of ethyl dimethylaminopropyl carbodiimide hydrochloride were added and the mixture was left to warm to room temperature. After stirring for a further 18 hours the solvent was removed by evaporation. The residue was dissolved in 1.3 l of dichloromethane and the solution was washed three times with 400 ml of saturated sodium hydrogen carbonate solution, dried over anhydrous magnesium sulphate and evaporated. The crude product was dried at room temperature under a vacuum to give 65.46 g of a pale brown foam. This was dissolved with warming in a mixture of 10 ml of ethyl acetate and 10 ml of hexane and the solution was flash chromatographed on silica gel while eluting with ethyl acetate/hexane (1:1) and collecting fractions of 250 ml. Product-containing fractions were combined and evaporated to give a white foam which, after crystallization from a mixture of ethyl acetate and 60-80 petroleum ether, gave 40.22 g (96.7%) of 1-[3-O-[N-(tert-butoxycarbonyl)-L-valyl]-5-[2(S)-(2,4-dichloro-5-methoxyphenoxy)-propionamido]-2,5-dideoxy-2-fluoro-β-D-arabinofuranosyl]-5-ethyluracil as a white crystalline solid, m.p. 117°-122° C.

(B) 40.22g (0.056mol) of 1-[3-O-[N-(tert-butoxycarbonyl)-L-valyl]-5-[2(S)-(2,4-dichloro-5-methoxyphenoxy)-propionamido]-2,5-dideoxy-2-fluoro-β-

D-arabinofuranosyl]-5-ethylu were dissolved in 400 ml of dry ethyl acetate. The solution was cooled to 0° C. and a cold saturated solution of hydrogen chloride in 800 ml of ethyl acetate was added. The solution was left to warm to room temperature and was stirred for 4 hours and then evaporated. The residue was dried at room temperature in a vacuum to give 37.0 g of an off-white foam. This was dissolved in 120 ml of distilled water and the solution was freeze-dried. The residue was dried at 60° C. in a vacuum to give 35.471 g (96.8%) of 1-[5-[2(S)-(2,4-dichloro-5-methoxyphenoxy) propionamido]-1,5-dideoxy-2-fluoro-3-O-L-valyl-β-D-arabinofuranosyl]-5-ethyluracil hydrochloride as a white solid. A sample was crystallized from hot isopropanol and gave a white crystalline solid, m.p. 132°–157° C. (dec.).

The 1-[5-[2(S)-(2,4-dichloro-5-methoxyphenyl)-propion-amido]-2,5-dideoxy-2-fluoro-β-D-arabinofuranosyl]-5-ethyluracil used as the starting material was prepared as follows:

(i) A mixture of 29.6 g (0.125 mol) of methyl (R)-2-trifluoro-methanesulphonyloxypropionate, 24.16 g (0.125 mol) of 2,4-dichloro-5-methoxyphenol and 17.52 g (0.127 mol) of potassium carbonate in 400 ml of acetonitrile was stirred under nitrogen and heated to 70° C. for 1 hour. The mixture was left to cool to room temperature and filtered. The filtrate was evaporated and the residue was partitioned between 400 ml of ethyl acetate and 400 ml of water. The separated organic phase was dried over anhydrous magnesium sulphate and evaporated to give 34.4 g (98.4%) of methyl (S)-2-(2,4-dichloro-5-methoxyphenoxy)-propionate as a pale yellow oil which crystallized on standing.

(ii) 125 ml (0.125 mol) of 1M sodium hydroxide solution were added to a solution of 34.9 g (0.125 mol) of methyl (S)-2-(2,4-dichloro-5-methoxyphenoxy)-propionate in 200 ml of ethanol. The solution was stirred at room temperature for 40 minutes and then adjusted to pH 1 with 2M hydrochloric acid. Most of the solvent was evaporated and the residue was partitioned between 400 ml of ethyl acetate and 400 ml of water. The separated organic phase was dried over anhydrous magnesium sulphate and evaporated to give 32.4 g (97.7%) of (S)-2-(2,4-dichloro-5-methoxyphenoxy)-propionic acid as a white solid, m.p. 114°–115° C.

(iii) 24.2 g (0.091 mol) of (S)-2-(2,4-dichloro-5-methoxyphenoxy)-propionic acid were suspended in a mixture of 150 ml of toluene and 0.5 ml of dimethylformamide and the suspension was stirred under nitrogen. 15.0 ml (0.17 mol) of oxalyl chloride were added, with vigorous evolution of gas occurring. The mixture was stirred for 1 hour to give a homogeneous solution. The solvents were removed by evaporation, the residue was taken up in 100 ml of diethyl ether and the solution was added to a solution of 24.6 g (0.090 mol) of 1-(5-amino-2,5-dideoxy-2-fluoro-β-D-arabinofuranosyl)-5-ethyluracil in 290 ml of 0.31M sodium hydroxide solution. The heterogeneous mixture was shaken vigorously for 10 minutes to give a white precipitate which was filtered off and washed firstly with water and then with diethyl ether. The crude product was recrystallized from hot methanol to give 33.1 g (69.7%) of 1-[5-[2 (S)-(2,4-dichloro-5-methoxyphenoxy)-propionamido]-2,5-dideoxy-2-fluoro-β-D-arabinofuranosyl]-5-ethyluracil as a white crystalline solid, m.p. 195°–196° C.

EXAMPLE 2

(A) Coupling of 1-[5-[2(S)-(2,4-dichloro-5-methoxyphenoxy)-propionamido]-2,5-dideoxy-2-fluoro-β-D-arabinofuranosyl-5-ethyluracil with N-Boc-D-valine in a manner analogous to that described in Example 1(A) gave 1-[3-O-[N-(tert-butoxycarbonyl)-D-valyl]-5-[2(S)-(2,4-dichioro-5-methoxyphenoxy)-propionamido]-2,5-dideoxy-2-fluoro-β-D-arabinofuranosyl-5-ethyluracil as a white solid, m.p. 101° C. (dec.).

(B) Removal of the protecting group from 1-[3-O-[N-(tert-butoxycarbonyl)-D-valyl]-5-[2(S)-(2,4-dichloro-5-methoxy-phenoxy)-propionamido]-2,5-dideoxy-2-fluoro-β-D-arabino-furanosyl-5-ethyluracil in a manner analogous to that described in Example 1(B) gave 1-[5-[2(S)-(2,4-dichloro-5-methoxyphenoxy)-propionamido]-2,5-dideoxy-2-fluoro-3-O-D-valyl-β-D-arabino-furanosyl-5-ethyluracil hydrochloride as a white solid, m.p. 140° C. (dec.).

EXAMPLE 3

(A) Coupling of 1-[5-[2(S)-(2,4,6-trichloro-3-methoxyphenoxy)-propionamido]-2,5-dideoxy-2-fluoro-β-D-arabinofuranosyl]-5-ethyluracil with N-Boc-L-valine in a manner analogous to that described in Example 1(A) gave 1-[3-O-[N-(tert-butoxycarbonyl)-L-valyl]-5-[2(S)-(2,4,6-trichloro-3-methoxyphenoxy)-propionamido]-2,5-dideoxy-2-fluoro-β-D-arabinofuranosyl]-5 -ethyluracil as a white solid, m.p. 147°–149° C.

(B) Removal of the protecting group from 1-[3-O-[N-(tert-butoxycarbonyl)-L-valyl]-5-[2(S)-(2,4,6-trichloro-3-methoxy-phenoxy)-propionamido]-2,5-dideoxy-2-fluoro-β-D-arabino-furanosyl]-5 -ethyluracil in a manner analogous to that described in Example 1(B) gave 1-[5-[2(S)-(2,4,6-trichloro-3-methoxyphenoxy)-propionamido]-2,5-dideoxy-2-fluoro-3-O-L-valyl-β-D-arabino-furanosyl]-5-ethyluracil hydrochloride as a white solid, m.p. 150°–160° C.

The 1-[5-[2(S)-(2,4,6-trichloro-3-methoxyphenoxy)-propionamido]-2,5-dideoxy-2-fluoro-β-D-arabinofuranosyl]-5-ethyluracil used as the starting material was prepared as follows:

In an analogous manner to that described in Example 1(i)–(iii), by reacting methyl (R)-2-trifluoromethanesulphonyloxypropionate with 2,4,6-trichloro-3-methoxyphenol, hydrolyzing the resulting methyl (S)-2-(2,4,6-trichloro-3-methoxyphenoxy) propionate, converting the (S)-2-(2,4,6-trichloro-3-methoxyphenoxy)-propionic acid obtained into the acid chloride and coupling the latter with 1-(5-amino-2,5-dideoxy-2-fluoro-β-D-arabinofuranosyl)-5-ethyluracil there was obtained 1-[5-[2(S)-(2,4,6-trichloro-3-methoxyphenoxy)-propionamido]-2,5-dideoxy-2-fluoro-β-D-arabino-furanosyl]-5-ethyluracil as a white solid, m.p. 210°–211° C.

EXAMPLE 4

(A) Coupling of 1-[5-[2(S)-(2,4-dibromo-5-methoxyphenoxy)-propionamido]-2,5-dideoxy-2-fluoro-β-D-arabinofuranosyl]-5-ethyluracil with N-Boc-L-valine in a manner analogous to that described in Example 1(A) gave 1-[5-[2(S)-(2,4-dibromo-5-methoxyphenoxy)-propionamido]-3-O-[N-(tert-butoxycarbonyl)-L-valyl]-2,5-dideoxy-2-fluoro-β-D-arabinofuranosyl]-5-ethyluracil as a white solid, m.p. 101°–111° C.

(B) Removal of the protecting group from 1-[5-[2(S)-(2, 4-dibromo-5-methoxyphenoxy)-propionamido]-3-O-[N-(tert-butoxy-carbonyl)-L-valyl]-2,5-dideoxy-2-fluoro-β-D-arabinofuranosyl]-5-ethyluracil in a manner analogous to that described in Example 1(B) gave 1-[5-[2(S)-(2,4-dibromo-5-methoxyphenoxy)-propionamido]-2,5-dideoxy- 2-fluoro-3-O-L-valyl-β-D-arabinofuranosyl-5-ethyluracilhydrochloride as a white solid, m.p. 148° C. (dec.).

The 1-[5-[2(S)-(2,4-dibromo-5-methoxyphenoxy)-propionamido]-2,5-dideoxy-2-fluoro-β-D-arabinofuranosyl]-5-ethyluracil used as the starting material was prepared as follows:

In an analogous manner to that described in Example 1(i)–(iii), by reacting methyl (R)-2-trifluoromethanesulphonyloxypropionate with 2,4-dibromo-5-methoxyphenol, hydrolyzing the resulting methyl (S)-2-(2,4-dibromo-5-methoxyphenoxy)propionate, converting the (S)-2-(2,4-dibromo-5-methoxyphenoxy)-propionic acid obtained into the acid chloride and coupling the latter with 1-(5-amino-2,5-dideoxy-2-fluoro-β-D-arabinofuranosyl)-5-ethyluracil there was obtained 1-[5-[2(S)-(2,4-dibromo-5-methoxy-phenoxy)-propionamido]-2,5-dideoxy-2-fluoro-β-D-arabino-furanosyl]-5-ethyluracil as a white solid, m.p. 223°–224° C.

EXAMPLE 5

(A) Coupling of 1-[5-[2(R)-(2,4-dichloro-5-methoxyphenoxy)-propionamido]-2,5-dideoxy-2-fluoro-β-D-arabinofuranosyl]-5-ethyluracil with N-Boc-L-valine in a manner analogous to that described in Example 1(A) gave 1-[3-O-[N-(tert-butoxycarbonyl)-L-valyl]-5-[2(R)-(2,4-dichloro-5-methoxyphenoxy)-propionamido]-2,5-dideoxy-2-fluoro-β-D-arabinofuranosyl]-5-ethyluracil as a white solid, m.p. 110° C. (dec).

(B) Removal of the protecting group from 1-[3-O-[N-(tert-butoxycarbonyl)-L-valyl]-5-[2(R)-(2,4-dichloro-5-methoxyphenoxy)-propionamido]-2,5-dideoxy-2-fluoro-β-D-arabinofuranosyl]-5-ethyluracil in a manner analogous to that described in Example 1(B) gave 1-[5-[2(R)-(2,4-dichloro-5-methoxyphenoxy)-propionamido]-2,5-dideoxy-2-fluoro-3-O-L-valyl-β-D-arabinofuranosyl]-5-ethyluracil hydrochloride as a white solid, m.p. 153°–160° C.

The 1-[5-[2(R)-(2,4-dichloro-5-methoxyphenoxy)-propionamido]-2,5-dideoxy-2-fluoro-β-D-arabinofuranosyl]-5-ethyluracil used as the starting material was prepared as follows:

In an analogous manner to that described in Example 1(i)–(iii), by reacting methyl (S)-2-trifluoromethanesulphonyloxypropionate with 2,4-dichloro-5-methoxyphenol, hydrolyzing the resulting methyl (R)-2-(2,4-dichloro-5-methoxyphenoxy)propionate, converting the (R)-2-(2,4-dichloro-5-methoxyphenoxy)-propionic acid obtained into the acid chloride and coupling the latter with 1-(5-amino-2,5-dideoxy-2-fluoro-β-D-arabinofuranosyl)-5-ethyluracil there was obtained 1-[5-[2(R)-(2,4-dichloro-5-methoxyphenoxy)-propionamido]-2,5-dideoxy-2-fluoro-β-D-arabinofuranosyl]-5-ethyluracil as an off-white solid, m.p. 151°–156° C.

The following Example illustrates a pharmaceutical preparation containing a compound of formula I.

EXAMPLE A

Tablets containing the following ingredients may be produced in a conventional manner:

| Ingredient | Per tablet |
| --- | --- |
| Compound of formula I | 100 mg |
| Lactose | 70 mg |
| Maize starch | 70 mg |
| Polyvinylpyrrolidone | 5 mg |
| Magnesium stearate | 5 mg |
| Tablet weight | 250 mg |

We claim:

1. A compound of the formula

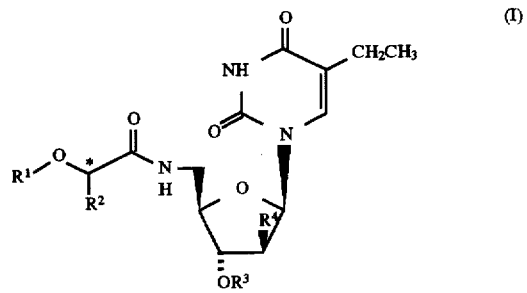

(I)

wherein

R¹ represents aryl,

R² represents lower alkyl,

R³ represents an acyl residue of an amino acid,

R⁴ represents hydrogen or fluorine, and the asterisk denotes that the configuration at the carbon atom indicated thereby is (S) or (R), and pharmaceutically acceptable acid addition salts thereof.

2. A compound according to claim 1, wherein the configuration at the carbon atom indicated by the asterisk is (S).

3. A compound according to claim 1, wherein R¹ represents a substituted phenyl group.

4. A compound according to claim 3, wherein the substituted phenyl group is 2,4-dichloro-5-methoxyphenyl.

5. A compound according to claim 1, wherein R² represents methyl.

6. A compound according to claim 1, wherein R³ represents an acyl group derived from a natural α-amino acid.

7. A compound according to claim 6, wherein R³ represents L-valyl.

8. A compound according to claim 1, wherein R⁴ represents fluorine.

9. A compound according to claim 3, wherein R² is methyl, and R³ represents a natural α-amino acid.

10. The compound 1-[5-[2(S)-(2,4-Dichloro-5-methoxyphenoxy)-propionamido]-2,5-dideoxy-2-fluoro-3-O-L-valyl-β-D-arabinofuranosyl]-5-ethyluracil.

11. The compound 1-[5-[2(R)-(2,4-Dichloro-5-methoxyphenoxy)-propionamido]-2,5-dideoxy-2-fluoro-3-O-L-valyl-β-D-arabinofuranosyl]-5-ethyluracil.

12. A pharmaceutical composition comprising as the therapeutically active ingredient at least one compound of formula I, claim 1, together with a compatible pharmaceutical carrier.

13. A process for the manufacture of the compounds of formula I, claim 1, which process comprises a) reacting a compound of the general formula

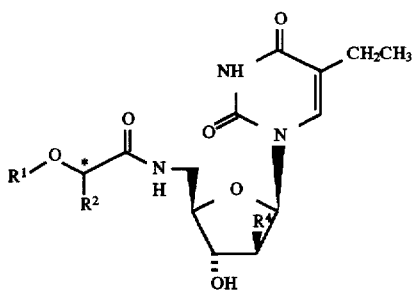

(II)

wherein

R¹ represents aryl,

R² represents lower alkyl,

R⁴ represents hydrogen or fluorine, and the asterisk denotes that the configuration at the carbon atom indicated thereby is (S) or (R), with an N-protected amino acid, and b) cleaving off the N-protecting group.

14. A method for the therapy of a viral infection comprising administering to the host a therapeutically effective amount of at least one compound of formula I, claim 1.

* * * * *